US007593819B2

(12) United States Patent
Hunkapiller et al.

(10) Patent No.: US 7,593,819 B2
(45) Date of Patent: Sep. 22, 2009

(54) INTERNAL CALIBRATION STANDARDS FOR ELECTROPHORETIC ANALYSES

(75) Inventors: Timothy Hunkapiller, Mercer Island, WA (US); Cheryl Heiner, La Honda, CA (US); Curtis Gehman, Pasadena, CA (US); James Labrenz, San Francisco, CA (US); Shiaw-Min Chen, San Jose, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 983 days.

(21) Appl. No.: 10/193,776

(22) Filed: Jul. 11, 2002

(65) Prior Publication Data

US 2003/0032042 A1 Feb. 13, 2003

Related U.S. Application Data

(60) Provisional application No. 60/304,934, filed on Jul. 11, 2001.

(51) Int. Cl.
*G01N 33/50* (2006.01)
*C12Q 1/68* (2006.01)
(52) U.S. Cl. ............................................. 702/20; 435/6
(58) Field of Classification Search ................ 422/50; 435/6; 702/20
See application file for complete search history.

(56) References Cited

U.S. PATENT DOCUMENTS

| 4,660,151 | A |  | 4/1987 | Chipman et al. |
| 5,119,316 | A |  | 6/1992 | Dam et al. |
| 5,365,455 | A |  | 11/1994 | Tibbetts et al. |
| 5,523,217 | A |  | 6/1996 | Lupski et al. |
| 5,541,067 | A |  | 7/1996 | Perlin |
| 5,580,728 | A |  | 12/1996 | Perlin |
| 5,633,129 | A |  | 5/1997 | Karger et al. |
| 5,871,628 | A |  | 2/1999 | Dabiri et al. |
| 5,916,747 | A |  | 6/1999 | Gilchrist et al. |
| 6,054,268 | A |  | 4/2000 | Perlin |
| 6,110,683 | A |  | 8/2000 | Reynolds et al. |
| 6,131,072 | A |  | 10/2000 | Holden et al. |
| 6,195,449 | B1 |  | 2/2001 | Bogden et al. |
| 6,251,591 | B1 |  | 6/2001 | Wu et al. |
| 6,397,150 | B1 | * | 5/2002 | Izmailov ...................... 702/20 |
| 6,681,186 | B1 | * | 1/2004 | Denisov et al. ............. 702/151 |

FOREIGN PATENT DOCUMENTS

| WO | WO 97/22942 A1 | 6/1997 |
| WO | WO 98/00708 A1 | 1/1998 |
| WO | WO 98/11258 A1 | 3/1998 |
| WO | WO 98/54669 A1 | 12/1998 |
| WO | WO 99/53423 A1 | 10/1999 |
| WO | WO 00/16087 A1 | 3/2000 |

OTHER PUBLICATIONS

Yoshimoto et al, Multiple Fluorescence-Based PCR-SSCP Analysis, 1994, BioTechniques, vol. 16, No. 2, pp. 296-300.*
Jane S. Ellison, Fluorescence-Based Mutation Detection, 1996, Molecular Biotechnology, vol. 5, pp. 17-31.*
Allex et al., "Improving the Quality of Automatic DNA Sequence Assembly using Fluorescent Trace-Data Classifications," Appears in Proceedings of the Fourth Int'l. Conf. On Intelligent Systems for Mol. Bio. 3-14, St. Louis, MO: AAAI Press (1996).
Alphey, "DNA Sequencing," The Introduction to Biotechniques Series, BIOS Scientific Publishers Ltd., pp. 63-79 (1997).
Ansorge et al., "Sequencing Reactions for ALF (EMBL) Automated DNA Sequencer" Ch. 36 from Methods in Molecular Biology, vol. 23:DNA Seq. Protocols, edited by Griffin, pp. 317-319, 326-355 (1993).
Ansorge et al. (edited), "DNA Sequencing Protocols" Ch. 3 from DNA Sequencing Strategies Automated and Advanced Approaches, pp. 105-125 (1997).
Blanchard et al., "DNA Sample Tracking Using Molecular Barcodes," Microbial & Comparative Genomics, Ninth Int'l. Genome Sequencing and Analysis Conf. Sep. 13-16, 1997.
Denisov et al., "TraceTuner™-Next Generation Base Calling," Paracel® A Celera Business, pp. 1-7, Sep. 2000.
Ewing et al., "Base-Calling of Automated Sequencer Traces Using Phred. I. Accuracy Assessment," Genome Research by Cold Spring Harbor Laboratory Press, pp. 175-185 (1998).
Ewing et al., "Base-Calling of Automated Sequencer Traces Using Phred. II. Error Probabilities," Genome Research by Cold Spring Harbor Laboratory Press, pp. 186-194 (1998).
Frazier et al., "Validation of the Applied Biosystems Prism™ 377 Automated Sequencer for Forensic Short Tandem Repeat Analysis," Electrophoresis, Service Development, Forensic Science Service, pp. 1550-1552 (1996).
Giddings et al., "A Software System for Data Analysis in Automated DNA Sequencing," Genome Research, vol. 8, Issue 6, pp. 644-665 (1998).
Haan et al., "Modelling Electropherogram Data for DNA Sequencing Using Variable Dimension MCMC," Proceedings, IEEE Int'l. Conf. On Acoustics, Speech and Signal Processing (ICASSP 2000), Istanbul Turkey, 6, 3542-3545 (Jun. 2000).
Hall, "Sequencing Using the Du Pont Genesis™ 2000 DNA Analysis System" Ch. 37 from Methods in Molecular Biology, vol. 23:DNA Sequencing Protocols, edited by Griffin pp. 357-371 (1993).
Halloran et al., "Sequencing Reactions for the Applied Biosystems 373A Automated DNA Sequencer" Ch. 35 from Methods in Biology vol. 23:DNA Sequencing Protocols, edited by Griffin, pp. 297-315 (1993).
Hawkins et al., "Non-Invasive 96 Lane Gels on ABI 377xl with Automated Lane-Tracking," Jun. 20, 1997 http://www.-seq.wi.mit.edu/development/96_Pub.html.

(Continued)

*Primary Examiner*—Christopher R Tate
*Assistant Examiner*—Deborah A. Davis

(57) ABSTRACT

The present teachings relate, among other things, to polynucleotide sequencing, fragment analysis and sample/lane tracking, and to polynucleotide sequencers and analyzers that employ optical detection techniques. Embodiments of the present teachings are described which include, for example, the addition of a calibration standard to a sequencing reaction. Information such as peak spacing and peak shape can he extracted from the standard.

1 Claim, 7 Drawing Sheets

OTHER PUBLICATIONS

Kelley, "Automated Dye-Terminator DNA Sequencing" Ch. 26, from Automated DNA Sequencing and Analysis edited by Adams et al., pp. 175-181 (1994).

Li et al., "Using a Neural Network for Lane-Tracking of DNA Sequencing Slab Gels," Journal of Biochemical and Biophysical Methods, pp. 65-74 (2000).

Liu et al., "Optimization of High-Speed DNA Sequencing on Microfabricated Capillary Electrophoresis Channels," Anal. Chem., pp. 566-573 (1999).

Pereira et al., "Statistical Learning Formulation of the DNA Base-Calling Problem and its Solution in a Bayesian EM Framework" Discrete Applied Mathematics, 104 (3) :229:58, 2000.

Roque-Biwer et al., "Expanding the Capability of Sequencing and Fragment Analysis by the Introduction of a $5^{th}$ dye on a Multiple Capillary Electrophoresis Instrument," Microbial & Comparative Genomics, vol. 3, p. C-92, Fall 1998.

Spurgeon et al., "Automated Referenced Fluorescent Sequencing of DNA Templates and its Application to Multiplex Sequencing," Genomics Mapping and Sequencing, p. 331, May 6-10, 1992.

Stover, "High-Throughput Genotyping," Life Science News, Amersham Pharmacia Biotech, pp. 1-2 (2000).

Urquhart et al., "Highly Discriminating Heptaplex Short Tandem Repeat PCR System for Forensic Identification," Biotechniques, vol. 18, No. 1, pp. 116-121 (1994).

Wang et al., "Computer-Enhanced Analysis of Multicomponent Fluorescence Spectra," presented at $4^{th}$ Int'l. Congress on Comp. Appl. in Fermentation Tech., Univ. of Cambridge, pp. 1-29, Sep. 25-29, 1988.

Zackrone et al., "$5^{th}$ Color Sample Identification and Automated Gel Analysis on the ABI 377" Microbial Comparative Genomics, Tenth Int'l. Genome Seq. and An. Conf., p. C-58, Sep. 17-20, 1998.

Zhang et al., "Comparative Study of Kalman Filtering, Synchronous Excitation and Numerical Derivative Techniques in Fluorimetry," Analytica Clinica Acta, pp. 281-286 (1993).

"ABI Prism® Lane Guide™ Lane Identifier Kit" Product Literature (1999).

"Basecalling" http://www.stat.berkeley.edu/users/terry/Classes/s260.1998/Week8b/week8b/node11.html.

"Genetic Identity," Internal Lane Standard 600 (ILS 600) 1996-1999 http://www.euro.promega.com/geneticidentity/datasheets/ils600.html.

New England BioLabs, Inc. Catalog, pp. 114-115 (2000-2001).

OE Reports, No. 193, Jan. 2000, http://www.spie.org/web/oer/january/jan00/cover2.html.

"PE Biosystems Introduces the ABI Prism® Lane Guide™ Lane Identification Kit with Novel Five-Dye, One-Lane Technology," News Release, Apr. 13, 2000, http://www.appliedbiosystems.com/molecularbiology/press_releases/377/index.html.

Strategene Catalog pp. 130-133, 240-242 (1997-1998).

User Bulletin ABI Prism® 377 DNA Sequencer, pp. 1-26, (1999).

* cited by examiner

Fig. 1A
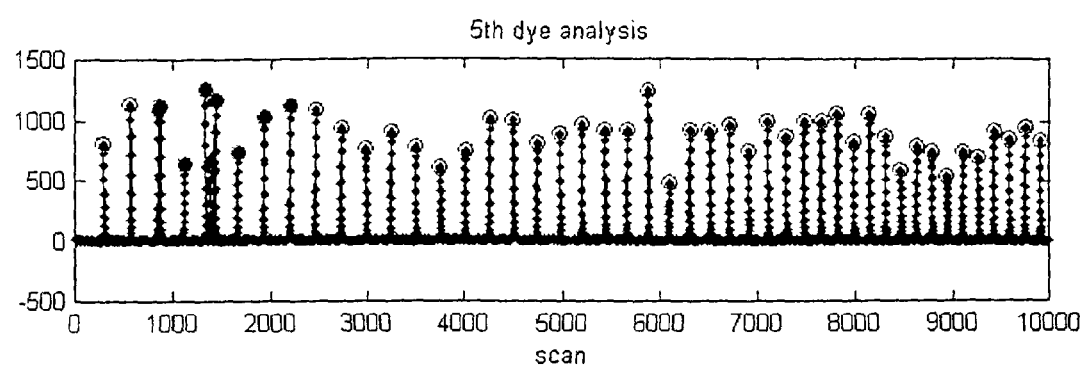
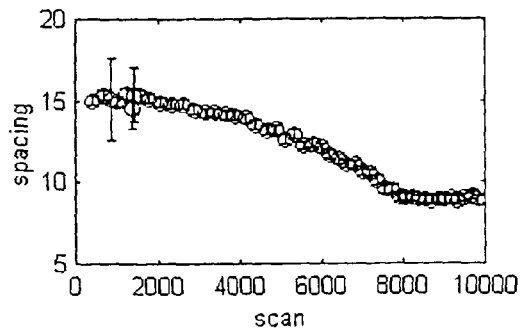
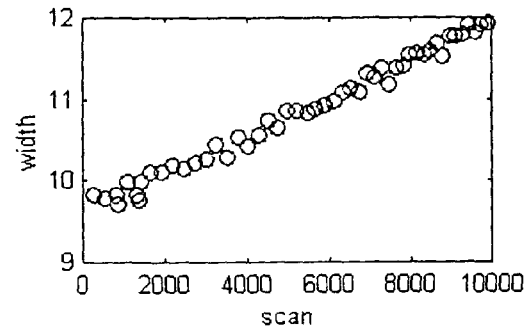
Fig. 1B
Fig. 1C

Sequencing Signals

5th dye Signals

INTERNAL CALIBRATION STANDARDS FOR ELECTROPHORETIC ANALYSES

This application claims priority to U.S. Provisional Patent Application No. 60/304,934 filed Jul. 11, 2001, which is incorporated herein by reference.

FIELD

The present teachings relate to polynucleotide sequencing and fragment analyses, and to polynucleotide sequencers and analyzers that employ optical fluorescence detection techniques.

REFERENCES

Hunkapiller, T. et al. (1991) Science 254 (5028):59-67.

R. G. Lyons, "Understanding Digital Signal Processing," Addison-Wesley, 1997.

See-Kiong Ng, Thesis: "Automating Computational Molecular Genetics: Solving the Microsatellite Genotyping Problem," Jan. 23, 1998, School of Computer Science, Carnegie Mellon University, Pittsburgh, Pa.

N. S. Wang, P. J. B. Rinaudo, T. J. McAvoy, "Computer-Enhanced Analysis of Multicomponent Fluorescence Spectra," presented at Fourth International Congress on Computer Applications in Fermentation Technology: Modelling and Control of Biotechnical Processes, University of Cambridge, UK, Sep. 25-29, 1988.

BACKGROUND

Automated DNA sequencing presents a number of challenges to the data analysis process. The input data can be highly variable and predictive models of data behavior are lacking, yet computer analysis routines are expected to produce highly accurate output data.

Base-calling is the data analysis part of automated DNA sequencing, which takes the time-varying signal of four fluorescence intensities and produces an estimate of the underlying DNA sequence which gave rise to that signal.

Generally, base calling software works by applying a "model" of various phenomena, such as diffusion and smearing, differences in mobility of the various dyes and sequence-specific variations in migration, to observed spectral data in order to predict the true behavior of the fragments and how they are separating. The more realistic the model, the better an algorithm can deconvolve the raw signal data into a representation of true fragment separation order and, hence, the sequence (and/or fragment size). The widely-used algorithms provide only very simple and approximate models.

Although each of these sources for improvement has been dealt with to some degree of success, it is clear that a more integrated approach is needed to make a breakthrough advancement over the current methods. Particularly useful would be a modification to the sequencing process that can provide an improved algorithm with the added information needed to develop a more refined view of the true data signal and a realistic model of the separating fragments.

A major source of basecalling error is the incorrect estimate of spacing, i.e., knowing when fragments associated with a particular base will cross the detector. This is especially noticeable in homopolymer regions late in the run; e.g., a run of say, 5 As can be incorrectly called as 6 As. Currently, a number of separate calibration runs and extensive analysis produce hard-coded spacing curves. However, variations in the applied running conditions or simply uncontrolled experimental variation can produce fragment separation profiles that deviate substantially from the hard-coded curves. A dynamic method of determining peak spacing that is robust to different run conditions would substantially improve basecalling accuracy late in the run.

The mathematical method or technique of deconvolution provides another opportunity to improve basecalling accuracy. Deconvolution attempts to explain raw data as series of known peak shapes and has been shown to adequately separate overlapping peaks. However, deconvolution can produce spurious peaks if the true peak shape and size is not known in advance. A method of measuring the peak shape and width of known isolated peaks would improve deconvolution methods, which in turn would substantially improve basecalling accuracy, particularly late (further along) in the run.

SUMMARY

Such problems are addressed by the teachings herein, for example, by way of the addition of a calibration standard to a polynucleotide analysis (e.g., sequencing or sizing) reaction. For example, one or both of peak shape and spacing information can be usefully extracted from the standard, providing a better model of fragment migration behavior, tailored to each individual experiment.

The present teachings provide for, among other things, one or more of: improved length or read, fewer basecalling errors, better assessment of data and experiment quality, and/or the ability to call data under a wide variety of experimental conditions.

Various aspects of the present invention relate to methods for calibrating an apparatus for the analysis of polynucleotides. In various embodiments, such a method can comprise:

(i) providing in an elongate separation channel of said apparatus: (a) a sample comprising a plurality of analyte polynucleotide fragments of unknown nucleotide sequence, each being associated with a first, second, third or fourth fluorescent label, and (b) an internal standard comprising a plurality of polynucleotide fragments of known nucleotide length, each being associated with a fifth (5th) fluorescent label; wherein each of said first, second, third, and fourth fluorescent labels are present in said sample, and further wherein said first, second, third, fourth and fifth fluorescent labels are spectrally distinguishable from one another;

(ii) electrophoretically separating the polynucleotide fragments;

(iii) (a) inducing fluorescence emission from the labels of the separating or separated polynucleotide fragments as they pass along a detection zone of said apparatus, (b) detecting the induced fluorescence emission, and (c) collecting data representing a fluorescence intensity trace for each of the detected labels;

(iv) locating peaks of the trace corresponding to said 5th label and determining at least one characteristic thereof, including at least one of peak shape and peak-to-peak spacing;

(v) generating a calibration model based at least in part on said at least one characteristic, and applying said model in locating and analyzing peaks corresponding to said first, second, third and fourth labels.

In various embodiments, such a method can further comprise making base calls for the analyte polynucleotide fragments of unknown nucleotide sequence.

These and various other embodiments are set forth in the following description, drawings, and appended claims.

BRIEF DESCRIPTION OF THE DRAWINGS

Exemplary structure and manner of operation of the present teachings, together with various objects and advantages thereof, are set forth in the following description taken in conjunction with the accompanying drawings, in which identical reference numerals identify like or similar elements, and in which:

FIG. 1A is an electropherogram representing data generated via a simulated 5th-dye electrophoresis run. The x-axis is scan number, and the y-axis is fluorescent amplitude, in arbitrary units. Regularly spaced peaks are identified by open circles, and patterned peaks are identified with closed circles.

FIG. 1B is a curve, estimated from the 5th-dye ladder of FIG. 1A, showing the spacing peak-to-peak as a function of scan number. The spacing is also reported in scan number.

FIG. 1C is a curve, estimated from the 5th-dye ladder of FIG. 1A, showing the width of each peak, in scan number, as a function of scan number. The width is measured as the full width at half the peak's maximum height (FWHM).

DESCRIPTION OF VARIOUS EMBODIMENTS

Figure 2:
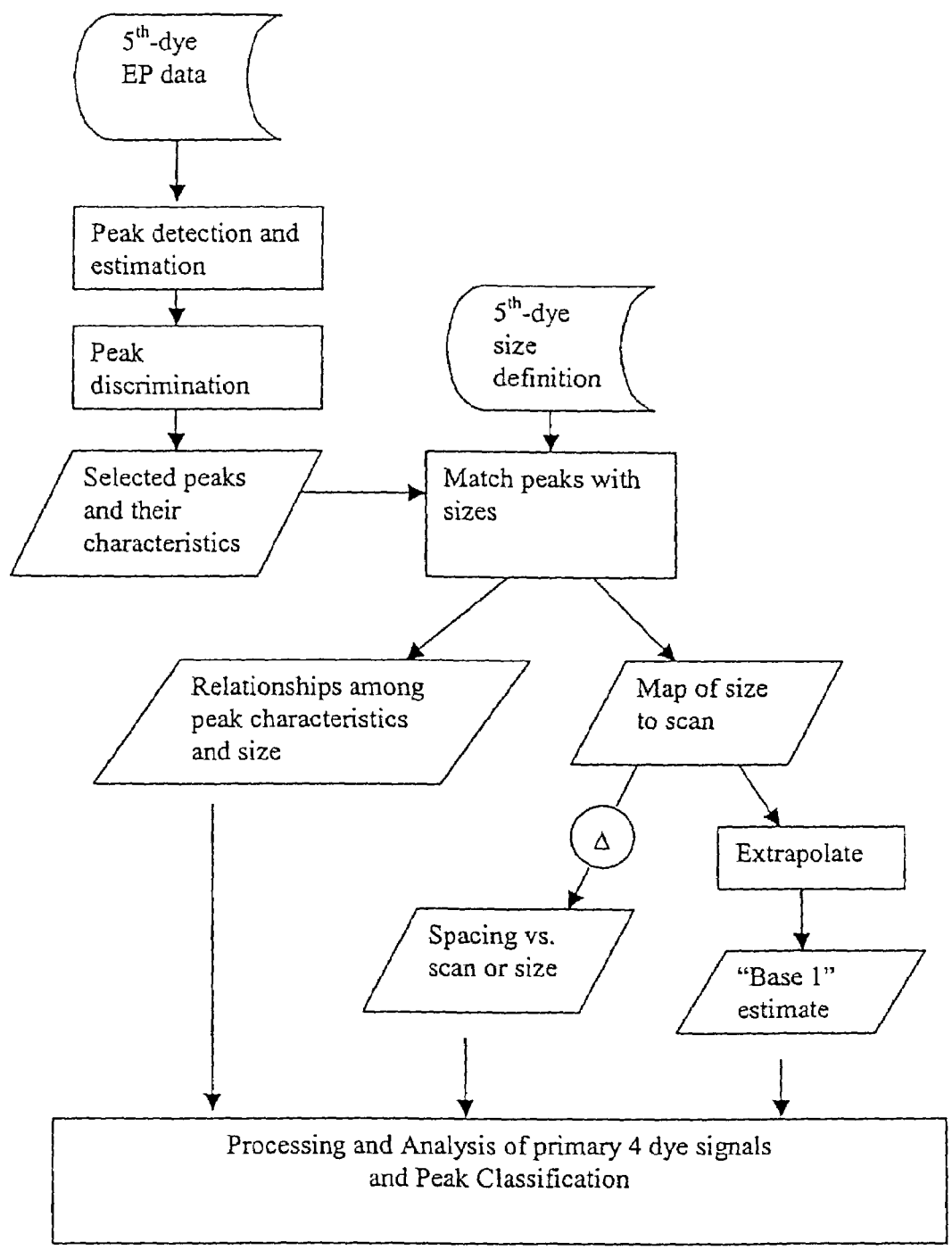
FIG. 2 is a flowchart showing steps contemplated by an embodiment of the present teachings.

Reference will now be made to various embodiments, examples of which are illustrated in the accompanying drawings. While the present teachings will be described in conjunction with various embodiments, it will be understood that they are not intended to limit the present teachings to those embodiments. On the contrary, the present teachings are intended to cover various alternatives, modifications, and equivalents, as will be appreciated by those of skill in the art.

With the highly-evolved detector capabilities of modern sequencers (e.g., the ABI Prism® 3700, 3100 and 377 DNA Analyzers from Applied Biosystems (Foster City, Calif.)), we are no longer limited to the four-color detection scheme typically used in DNA sequencing and fragment analysis. Therefore, standards labeled with different or "5th" dyes can be added to the same separation lane as samples, and detected along with the basic four currently used for sequencing or sizing reactions. These "internal" standards can then be used for tracking, signal analysis and/or sizing functions, etc. In various embodiments, an internal standard, as provided herein, comprises a set of labeled molecules, such as polynucleotide fragments of known size, that can be used to estimate the number of bases to be found within a given separation time interval as well as a more accurate peak shape model for that region (lane and migration time) of the gel.

While much of the present description is focused on 5th-dye standards in the context of capillary-based systems, it should be appreciated that slab gel-based devices can incorporate the present teachings, as well. Also, although much of the present description describes the use of one 5th-dye standard at a time, it should be appreciated that there is no inherent limitation to using more than one extra dye per lane (e.g., a 6th dye, a 7th dye, or more), with the ultimate number primarily depending on the process need and the spectral separation of the available dyes.

Implications for Sequencing/Mapping/Allele Detection

The present teachings provide for the inclusion in the sequencing lane (capillary, channel, gel track) of an internal standard that will permit a more accurate model of the underlying signal, allowing for a more precise deconvolution of base peaks. The standard can provide, for example, one or more of:

A spacing curve for determining how many bases should be in a given separation interval;

A lane/capillary/track and experiment-specific peak shape model (e.g., for deconvolution of the sample data);

Using total signal, peak shape and base line between standard peaks, a more accurate base line prediction;

Using calibrated peak shapes and base lines, a more accurate relative quantitation estimate between peaks and experiments as well as in mixed-base (e.g., heterozygote) analysis;

Calibration for mobility correction;

A start point (i.e., base 1) indicator;

A barcode-like sample/experiment tracking label;

Quality assessment (QA) indicator for sample loading and device status; and/or

Normalization and quantitation standards.

In various embodiments, a standard comprises a known set of molecules labeled with a fluor spectrally distinct from the four color set used for sequencing and/or fragment sizing. In certain embodiments, standards in accordance with the present teachings are capable of migrating in a fashion that can model that of sequencing-labeled DNA fragments and provide a similar peak shape upon detection. A standard in accordance with the teachings herein can, for example, be loaded with one or more lanes of labeled sequence reaction or sizing experiment and the extra or 5th dye color data returned for such lane(s) along with the conventional four color set. Using information provided by the 5th-color standard, a model for peak shape, baseline, migration, relative mobility, and/or relative sample quantity can be built uniquely for each lane and run condition combination. Such models permit the realization of a number of advantages over prior methods including, not only absolute longer read length potential, but faster run times for comparable read lengths as they can compensate for the reduced gel resolution of faster gels. This hybrid approach can greatly increase the true throughput (of finished data) of sequencing, reducing the cost per finished base and making sequencing accessible to more users. Also, the better signal model can allow for a more accurate binning function (a 1a TraceTuner™—Paracel; Pasadena, Calif.) for greater precision in quality value assessments and heterozygous discrimination. QA of the experimental process and machine status can be tracked knowing the specific standard and amount to be delivered to particular lanes.

The present teachings can find use in any number of environments; for example, very high-throughput groups, groups interested in long reads for finishing jobs, those in regulated environments in need of high "accuracy" and "precision"

(screening and diagnostics) and those interested in mixed sequencing strategies for discovery or diagnostics.

Although lane tracking is generally not a need for capillary instruments, there is still a huge installed base of gel-based systems, such as the ABI Prism® 377 (Applied Biosystems; Foster City, Calif.). Advantageously, a 5th dye standard can provide for much better lane discrimination, hence, tracking (i.e., tracing and isolating the fragments of a single sample as they migrate past the detectors). This, in turn, can facilitate denser sample loading, eliminate onerous manual re-tracking and enable various sequencing models (e.g., sequencing from both ends of the same clone) that are currently of little value on gel machines due to poor sample-to-lane referencing. It can also provide a method to either correct lane anomalies (from defective wells, etc.) or just pick a single (best) point for tracking so that band anomalies do not distort resolution. As the density of lanes increases, this can help to reduce the signal degradation of overlapping signal. One embodiment of the present invention employs different standard fragment sets in neighboring lanes (at least two alternating) or staggered loading. Using this approach, the number of lanes that can be resolved on a single gel can increase dramatically.

While lane tracking typically has little relevance to capillary systems, differential standards do have implications for template/reaction set tracking. Basic template labeling can greatly facilitate large-scale directed or double-end sequencing strategies by eliminating results mislabeling. This, in turn, reduces the demand on down-stream assembly programs, further reducing the amount of sequences to be done before a project has value. It also provides for more assurance in screening, diagnostic and forensic applications where clone identification is critical. For example, a set of 5th dye-labeled sizing fragments can provide for a complete 32 bit (or more) bar coding of all template samples. In one embodiment, microtiter plates are manufactured with bar codes pre-added to the wells. Such bar codes can help assure unique sample identification, even between different labs. This could be particularly useful in the maintenance of clinical samples.

Such sample tagging can find use in physical mapping samples, as well. For example, addition of a tag at the earlier template level can facilitate coordination of clone fingerprinting with subsequent sequencing (mapped-low pass sequencing strategies). It might be noted that sample ID is probably even harder for the subclone mapping projects (they need a high throughput as well as a highly automatable method for tracing which subclones to pick to sequence). The integrated sizing standards described herein can provide the same enhancement for sizing as the current GeneScan® (Applied Biosystems; Foster City, Calif.) methods do, but provide greater throughput (samples/lane). Also, the ability to better understand a signal (for correction, deconvolution, etc.), permitted by the present invention, can be just as useful for any sizing process, particularly the messier peak data of STR mapping and Type IIs enzymatic mapping of larger clones.

One important implication of a 5th dye system is the flexibility it provides to modify and improve protocols and run conditions. Tweaking, retraining and/or recalibration of the base calling software for each new matrix, dye set or separation time can be greatly minimized or eliminated. Preferred software, for use with the present invention, is adapted to use essentially any new internal standard included. The software is preferably configured to take as run-time parameters, the color to look for, the fragment pattern to look for, the sizes to associate with the pattern, peak-shape transformation functions and any composition-specific normalization factors (discussed below). The registration of the standard has another implication, as well. It can be used to better estimate the first base position of the sample. Not only does this allow for more accurate and longer early reads, it facilitates better identification of leading vector or tag sequence for elimination, classification, etc.

Better peak shape and baseline models, which can be realized by way of the present invention, can aid considerably in the relative quantification critical to mixed sequencing needs (relative frequency measurements). This can be useful in both SNP frequency analysis and mining as well as diagnostics (for somatic variation).

Technical Implications

Dye (Label) Properties:

The four dyes conventionally used for sequencing represent a compromise between the requirements for a convenient excitation frequency (usually a common frequency for all dyes unless multiple light sources or a non-laser source is used), enough separation in their emission frequencies, signal strength, similar size/mobility profiles, enzyme compatibility, sequence-specific dye interactions (affecting mobility differences) and manufacturability. While any new 5th dyes are not excused from all of these concerns, their requirements are not, in general, quite as restrictive.

While its excitation frequency is preferably in the same range as the conventional set (given a common laser), the emission frequency is preferably well removed from sequencing dyes. While this is preferable for the sequencing dyes as well, the 5th dye is not constrained to be mobility matched. Therefore, the choice can emphasize this separation. This can be particularly important, in fact, to maintain the best noise profile in the total signal. Relative mobility has to be only reasonably similar (can be off by multiple bases). It is only important that the shifts are consistent and predictable.

Labeled Molecule Properties:

Desirable characteristics of the molecule to be labeled with the 5th dye reagent depend at least in part on the intended use of the labeled set. As contemplated in an embodiment herein, two primary characteristics of the molecule to be labeled (in conjunction with how it interacts with the labeling agent) are to produce consistent results and to maintain typical peak behavior—shape is preferably about the same as a similarly sized sequence fragment—while allowing the fewest molecules to be loaded. While certain embodiments contemplate that it is easier, at least initially, to label a nested set of DNA fragments, there is no inherent limitation on the molecule(s) used. Lane and sample tracking, for example, have no real shape or size requirements, just a consistent banding. Also, in addition to a 5th dye, the present invention contemplates the use of a sixth (or more), as long as the spectral resolution is provided. Signal analysis and sample tracking do not have to be a combined function. The fragment can be labeled with multiple dyes if signal is improved without compromising mobility consistency. The peak shape does not have to be identical to a similar-sized sample fragment as long as it can be predictably mapped into what one of that size would look like. This ability to map between peak shapes can be useful for extrapolating confidence value metrics to new protocols without having to run a lot of calibrating sequences.

Certain embodiments herein contemplate the use of 5th dye-labeled DNA fragments. Examples of DNA-based ladders, contemplated by the present invention, may include one or more of the following properties:

single base sequencing reaction of a known standard (e.g., T ladder);

set of PCR fragments of known length (in one embodiment, a set that is nested with a common end, as opposed to a series of unrelated sequences);

bacterially-amplified clone inserts—e.g., a set of S1 nuclease products;

a single oligo with sticky ends self ligated to generate a ladder;

a set of entirely synthetic nested sequences designed for particular properties of dyad structure, labeling facilitation, manufacturability, mobility consistency, composition, etc.

Any of the above can provide a set of DNA fragments of known, representative sizes that can be readily labeled. It is not critical that the size differences between the rungs of the ladder be consistent (the same). In fact, some inconsistency can be useful for registering the fragment data with the sizing information provided to the base caller. However, the consistency of a ladder made up of increments of the same sequence can be attractive (the ligated ladder model). Since sequences of the same length and even the same labeling can migrate slightly differently due to sequence-specific mobility issues (a pyrimidine-rich sequence will tend to migrate faster than a purine-rich sequence), the sequence of the increments can be chosen to reflect an "average" sequence. A compensation factor can be included in the base caller when estimating the number of bases between two standard points depending on the estimated base composition in that region relative to the standard fragment. The standard sequence is preferably designed to avoid or minimize secondary structure problems that lead to anomalous and unpredictable local fragment mobility.

Labeling techniques employable with the present invention can be, for example, some form of single base extension with dye-labeled terminators, the use of labeled primers in amplification schemes or the direct incorporation of labeled end fragments in any ligation method. The particular method chosen will reflect a balance between the ease of labeling, the ease of fragment generation and the implication the different labeling (terminator or primer) has for peak shape modeling.

According to various embodiments, the labeled standard molecules are designed and/or selected to provide a directly analogous mobility curve to the fragments being sized. Various embodiments achieve the best signal model by utilizing labeling that is similar to the actual sequencing or sizing reaction labeling. For example, much of sequencing is done with labeled terminators. Standard fragments, according to the present invention, can be labeled the same way. This can be complicated by the nature of sequence-specific interactions of the label with the sample; labeled primers all have the same local sequence next to the dye while terminator labels are usually next to different local sequences. As provided in embodiments herein, the standard DNA fragments can be designed to have the same local end sequence to minimize this problem (e.g., a ligated ladder model, or clone made from a ligated ladder or a custom-designed, mostly random sequence with short, common elements adjacent to the base to be labeled to be used in dideoxy sequencing reactions).

According to various embodiments, as little of the standard is loaded as possible in order to decrease costs as well as not decrease resolution because of loading volume and overload distortions, but enough is loaded to provide representative peak characteristics. The actual peak sizes of the standard can be significantly less than the sequencing peaks, even more so as the spectral separation improves, because the base caller can know what to look for and basically where to look. Therefore, in many instances as little as one tenth the molar quantity of a regular sequence reaction load will suffice, and in some cases less. It is noted that, as users dilute reaction mixtures, absolute signal may become a problem, requiring more standard to be included. Since the ladder molecules do not have to precisely reflect the mobility offsets of the normal dye/sequence fragment sets (it is the relative difference between fragments not the absolute size of the fragments that is important), multi-labeled fragments can be used to increase the signal strength so that even less standard can be loaded.

The Ladder Density

In embodiments of the present invention, preferred ladders of the present invention provide fully separated (clear base line) peaks over their length range, while having no more than is required to provide sufficient separation of the 5th dye-labeled fragments for the generation of mobility (migration vs. gel run-time) profile per lane. Such ladders can be experimentally determined. In one embodiment, a ladder on the order of 10-50 (e.g., 16, 18 or 20) is employed. It should be appreciated that the ladder does not have to be regular, i.e., the first few hundred bases or so may have a density of every 50 bases while the later sizes might be closer to 10. Also, even if the ladder is more or less regular, the differences between marker peaks positions do not have to be exactly the same, just known precisely. Some irregularity, in fact, can prove useful when registering the data to some absolute size standard. Also, having more fragments does not mean each has to be used: For example, a moving average can be calculated by using overlapping sets of two interval markers. A selection can be made from the standard that best meets the current experimental needs.

Since there really is no actual standard size DNA molecule (two fragments with the same number of bases will still migrate differently—sometimes dramatically—because of composition differences and sequence-specific interactions with the dye itself), it may be desirable to adjust and test for local composition extremes. One embodiment provides that it is preferred to maximize the density of the ladder (given loading and manufacturability requirements) so that moving averages can be used. Both a longer and shorter interval can be applied when calculating the estimated number of bases to be looked for in a region. For example, this could involve using a ten base ladder to provide both a ten base distance and a 50 base difference to get a best "average" spacing curve for the unknown data. This would be useful, for example, when the interval sequences of the standard were different.

Signal Correction

In certain embodiments, the standard dye employed is selected to provide for the greatest discrimination between the emission signals of the sequencing dyes and itself. This can be useful, for example, to provide for the best ID of its signal, as well as to reduce the noise inherent in the multi-component analysis. It can also provide a tool for better characterization of what the true signal properties and base line are. The signal is preferably great enough to provide peak shapes representative of true sample signal. The standards run under different experimental conditions can also provide a calibration (learning) model for new, untested conditions. Calibration models derived from one or more independent experiments could be extracted and used to provide models for similar experiments even without the 5th dye being included with these new experiments.

It should be noted that 5th dye peaks do not have to give precisely the same peak shapes as sequencing fragments. However, they are preferably consistent enough to make an appropriate extrapolation. Being able to do this transformation, also provides a method to predict the expected experimental peak shape using 5th dye peak data run under novel conditions that have not yet been trained for. This could be done dynamically (during the same "run") or a utility and process could be provided to extract data from a known sequence (a T reaction of a vector sequence, for example) run with a new protocol and map a shape-reference model to the internal standard for use in real experiments run under that protocol.

Use with Flat Gel Systems

For slab gel-based systems, provided that the software can use gel-wide information (i.e., include data from other lanes/gel regions separate from that of the individual lane being interpreted) when determining the migration profile of a particular lane, only some number of lanes are required to include this ladder. An interpolation can provide "virtual" standard profiles for the intervening lanes.

Lane Tracking

For flat gel machines it is useful to provide signals that run the length of the gel in order to facilitate lane tracking. This can be provided by a modification of the sizing standard. If every lane is loaded with the same size standard, then there is much less advantage for lane tracking (mitigated somewhat if the lanes are loaded asynchronously to offset adjacent lanes). However, if neighboring lanes have different sets of sizing fragments (for different patterns of band spacing), lane tracking software can use this information to follow up a lane and keep within the appropriate fragment set. Unlike the suggestion above about not loading a sizing standard in every lane, one embodiment of this scheme requires each lane to have a signal. For example, a minimum of two sets can be employed, alternately loaded. Another embodiment contemplates the use of three (or more) sets.

In various embodiments, a single complete set of sizing markers is divided into three subsets (divided in a way that no two consecutive sizes are in the same set) and the full gel analysis described above is used. Essentially, every three lanes, in this embodiment, provide all the size ranges for the lanes in their neighborhood and still provide lane-specific patterns to support tracking. With an expectation that adjacent lanes can not have the same standard banding pattern, the tracking/calling software can recognize "missing" lanes (i.e., where the loading failed), maintaining correct lane-to-sample correspondence.

Sample Tracking:

As previously indicated, the labeled molecule is not necessarily DNA. It can be any molecule that migrates within an appropriate size range on the gel and is relatively easily labeled. Depending on when it is added, it is also preferably friendly to and not harmed by the reaction conditions. A preferred model, in one embodiment, is that of a typical bar code (in fact, standard bar code coding schemes can be employed). In one embodiment, at least 16 bits, and more preferably 24-32, are used to provide a large enough sample number. The scheme can be binary (present or not present), or complex (e.g., trinary—0, 1× or 2× intensity). The first is simpler and requires no finesse while the second one requires fewer marker components (labeled elements) and less gel length for separation, but potentially a more complicated manufacturing process. In one embodiment, a starting motif (fragment banding pattern) is provided for each tag set so that each can be registered in the correct phase. It is noted that this can increase the number of bands required. At least 2-3 base-equivalent separation between size elements (bands) is preferred for base-line separation. In one embodiment, the total bar code is readable in no more than a 100 base separation range, preferably 50.

When to add the label (bar code) can be important to defining how best to do the sample coding, or at least how meaningful it is. In one preferred process, the sample ID is added at the moment a plaque or colony is picked. In one embodiment, the code accrues information as the processing of the sample proceeds (each step adding some number of bits that codes for that step). Alternatively, in another embodiment, a complete record of the process is kept by an information management system (LIMS).

In situations where the sample undergoes some form of amplification after its original picking, adding the code fragment set at the time of picking may not be optimal as it may be diluted out, not be isolateable with amplified template, and/or impact the amplification. Recognizing this, one embodiment provides the tag attached to a solid support (e.g., bead) that is added to the original plaque pick, which can then physically follow the template through the preparative and sequencing reactions with the appropriate protocol changes. The code set can then be clipped from the bead at gel loading time. A series of beads with different portions of the final code can be added during the process to track the sample history. In one embodiment, a series of multiply-labeled beads are pre-made and added in a combinatorial fashion a 1a hexamer sequencing.

In another embodiment, tag set addition is effected right after amplification. While this may result in loss of some referential integrity to the original pick, the present invention contemplates the use of a tracking program (e.g., linking an automated picker to the amplification device—if one is used) to minimize what is already a relatively minor problem. From this point, any division of the sample for different processing will be covered. The limit here is that the tag should not interfere with the sequencing reaction. In yet a further embodiment, which may be among the easiest to implement, each sequence reaction set is labeled before loading. This provides unique lane identification as well as referential integrity between a tube or well in the sequencing process and the gel loading process—two of the most significant points of error.

The present teachings further provide embodiments for lane identification (ID), as will now be described. In one embodiment, lane ID is provided by a barcode tag, as described above. Certain other, somewhat simpler, embodiments provide only for distinguishing lanes on a single gel (lane ID vs. sample ID). One method, as contemplated herein, is similar to the full sample ID embodiments, but requires fewer tagging components (namely, just enough bits to generate a number as large as the potential number of lanes (e.g., 7-8 bits)). Under circumstances where the sample ID is only added to completed sequencing reactions, and not to the template, this simpler method can be nearly as advantageous, except perhaps for those cases where the unused portion of the reaction set is saved for reloading. Even for those times the two ends of a template are sequenced, this method would be just as good as long as the template is aliquoted into separate sequencing reaction locations (wells in a microtiter plate, for example) directly so that the tracking is done by a database and not manually maintained/entered notes. Assuming that the samples are tracked (recorded) correctly when they are placed into the automated reaction process, these tags would provide the same level of discrimination. This would be useful to unambiguously distinguish lanes of data when reactions do not work and lane tracking might get confused as well as provide a link to same-template sequences.

Another potentially simple method for lane ID, contemplated by the present invention, integrates directly with the sizing/mobility tags. To provide lane-specific mobility predictions, essentially a sizing standard is required. To facilitate lane tracking, it can be useful to provide multiple such sizing standards such that adjacent lanes have different (but functionally equivalent) ones. Knowing that these defined markers are different for the length of the lanes can be used directly to keep the tracking in line. At the same time this provides a minimum designation for the lane ID. In the extreme, this embodiment calls for a different standard for every lane. However, 2, and preferably 3, standards loaded alternately can provide at least a consistency check for lane designation (e.g., if lane 4 has standard #1 loaded, but the tracking came back thinking lane 5 was lane 4 because reaction 4 did not work, then it would have standard #2 in it and the error would be recognizable). This method obviates the need for a barcode lane tag, but may not be as foolproof (and may not be as flexible in how tagged sequences are loaded on a gel). In one embodiment, it is preferred to combine both methods with only 2 size standards (assuming that template tagging is not employed).

For gel-based systems, provided the software can use gel-wide information when predicting a mobility profile for a particular lane, only some number of lanes have to have this ladder.

Since lane separation is not an issue for capillary electrophoresis sequencers, a simple, single-pattern 5th dye calibration standard can be included directly in sequencing chemistry kits. Employing such a kit, users will not be required to mix or add new reagents; the standard will be transparent to users.

Implications for Experimental Process

Beyond improving the ability to model and extract the best representation of the raw data and maintain referential integrity between samples and data, 5th dyes can aid in tracking the status and quality of individual experiments, comparing the results from different experiments, and the analysis of certain aspects of device (e.g., sequencer) performance. These can generally be discussed as quality control/assessment (QC/QA) functions and not only facilitate a more efficient overall experimental/industrial process, but generate the precise experimental descriptions needed for more regulated efforts.

Sample Injection/Loading Monitoring:

With current methods, when no signal is detected in a lane or capillary, it is unclear if the problem relates to the injection/loading process or the actual sequencing reaction. This can be better monitored when a known standard (5th dye) fragment set is included and loaded with the sequencing reaction product: the presence or absence of 5th dye signal can limit the possible error conditions. In this application the 5th dye fragment density can be any number, even one fragment per lane. An embodiment of this application is as the following:

A sequencing reaction product is combined with a 5th dye fragment set. This sample is loaded on an ABI Prism 3700 instrument and signal from each color channel is collected and extracted (in this case, channels one through five). The signal from the 5th dye channel is examined and is compared to the other four channels. If only the signal from the 5th dye channel is present, the sequencing reaction is presumed to have failed at some point. If channels one through four are present in signal strengths as expected (and/or as compared to other lanes/capillaries, if present (e.g., at least 50%, at least 75%, at least 85%, and/or at least 90% that of any other lanes, if present)), but no or much less 5th channel signal than expected (and/or as compared to others lanes/capillaries (e.g., less than 50%, less than 30%, less than 20%, and/or less than 10% that of any other lanes, if present)) is present, then the mixing process is suspect. If no or reduced 5th channel signal is combined with no or reduced sample channel strengths, then the loading has probably failed. In various embodiments, this function involves the ability to compare values between lanes as each lane should have a comparable amount of standard present.

Another common problem in sequencing is the presence of imperfections in the lane/capillary (e.g., bubble) or the loading well or injection volume. All of these can lead to distorted, and therefore, hard to discriminate bands and poor sequencing results even if the total sample signal is fine. This problem can be difficult to distinguish from simply poor or "dirty" sequencing reactions by looking at a trace of the various channels. However, since there is base line separation of the standard fragments (some distance between expected peaks), even distorted 5th dye bands are likely to be isolatable. Therefore, distorted (poorly shaped, too wide, etc.) bands can indicate the nature of the problem. In the best case, as indicated above, this information can be used to "clean up" the data well enough to get useable sequence data (by incorporating the actual peak shapes in the peak detection function).

Lane Signal Cross Talk:

The signal from one lane can bleed into the signal from adjacent lanes. In capillaries, this can be the result of poor calibration of the light source and/or the alignment of the capillaries and source/detector elements (e.g., scattered fluorescence from one lane is detected by the detector of another lane). In slab gels, this can be exacerbated by actual cross over of fragments between two lanes (poor loading, distorted gel, etc.). Overall, this signal cross talk can severely reduce the value of a lane. Cross talk is difficult to quantify due to the amount of "normal" signal at the same scan point and color channel. Therefore, it is difficult to distinguish this result from simply a poor sequence reaction. However, when a 5th dye fragment set is loaded with a sequencing reaction sample in either a capillary or a slab gel instrument, the signal cross talk can be determined independent of sequencing signals. This is basically possible because, particularly in capillaries, the standard bands will never exactly line up at the same time points in two separate lanes. In the most obvious cases, ghost peaks or shoulders in the 5th dye channel of one lane that correspond to signal peaks in an adjacent lane can be presumed to be cross talk. However, more diffuse signal scatter can simply raise the noise background. This signal leak may even be compensated for (subtraction of the bled signal before analysis). Just as important, it can be used to diagnose the instrument and its calibration. With basecallers "aware" of this phenomenon, automatic reports could be generated and system operators and support personnel could be notified. An embodiment of this application is as follows:

A sequencing reaction sample is combined with a 5th dye fragment set. This sample is loaded on an instrument (either capillary or slab systems). Signal from all five signal channels are collected for each lane. The amount of 5th dye signal at each time point is calculated for each lane. The ratio of cross talk is determined as the signal of the 5th dye signal in the adjacent lane divided by the 5th dye signal in the sample lane.

In situ Cross-Over (Resolution) Determination:

The resolving power of a separation matrix under particular conditions will determine how well fragments can be identified as separate from adjacent fragments. Many factors impact this resolution. An ability to calculate the resolving power of a particular process, therefore, can be useful in diagnosing experimental problems as well as predicting how much useful data can be gleaned. Resolution of a peak is often determined as the ratio of its distance to an adjacent peak and its width (calculated at half its height). This is sometimes referred as a cross-over plot—when the distance is less than half the width cross-over is achieved and the peaks are not considered isolatable. This is difficult to determine with only four-color sequencing reaction data because the density of bands lead to significant overlapping of peaks further into a run. Poor peak shape models combined with poor baseline determinations make the calculation of peak-to-peak distance and even their true heights problematic. However, when a set of moderate to high density, but still baseline resolved (2 to 10 fragments per 100 bases) 5th dye fragments is loaded with a sequencing reaction sample the system resolution can be determined independently of sequencing reaction sample signal. An embodiment of this application is as the following:

A sequencing sample is combined with a plurality of 5th dye fragments and is loaded with a sequencing reaction product. Signal from the 5th dye is collected and the peak location and peak width at half height of each peak is determined. Peak-to-peak distances are determined and the resolution determined.

Signal Strength Normalization.

Many applications of DNA fragment analysis require or could benefit from more quantitative descriptions. Because of differences in loading, detector sensitivities, etc. this is difficult, particularly between experiments. However, an internal standard of known quantity can provide a basis for normalization between experiments, even on different instruments. This provides a basis for at least relative quantitative comparisons. An embodiment of this application is as the following:

A sequencing sample is combined with a high density 5th dye fragments and is loaded with a sequencing reaction product. Signal from the sample channels as well as the 5th dye channel is collected and the total of each calculated over an appropriate window (number of peaks—one or more). The ratios of sample signal to 5th dye signal are determined. The relative quantity of the sample is determined as the ratio of this sample value between experiments.

Tracking System Performance:

When combined and tracked over time, the results of the above analyses can be used to monitor over all system (device plus process) performance. For example, since the amount and nature of the standard being loaded is known for each experiment, experiment-to-experiment (run-to-run) comparisons of signal strength, resolution, crossover, cross talk and peak shape consistency can be determined on an ongoing basis. This provides a description of changes that might reflect on the chemistry, the manipulative processes (e.g., loading), the matrix used (individual capillary, gel lot, etc.), calibration of the detection device, etc. Appropriate reporting procedures (software, etc.) can be constructed to illustrate these changes and associate them with predictive functions of process performance and/or maintenance intervention requirements.

Instrument System

Figure 3:
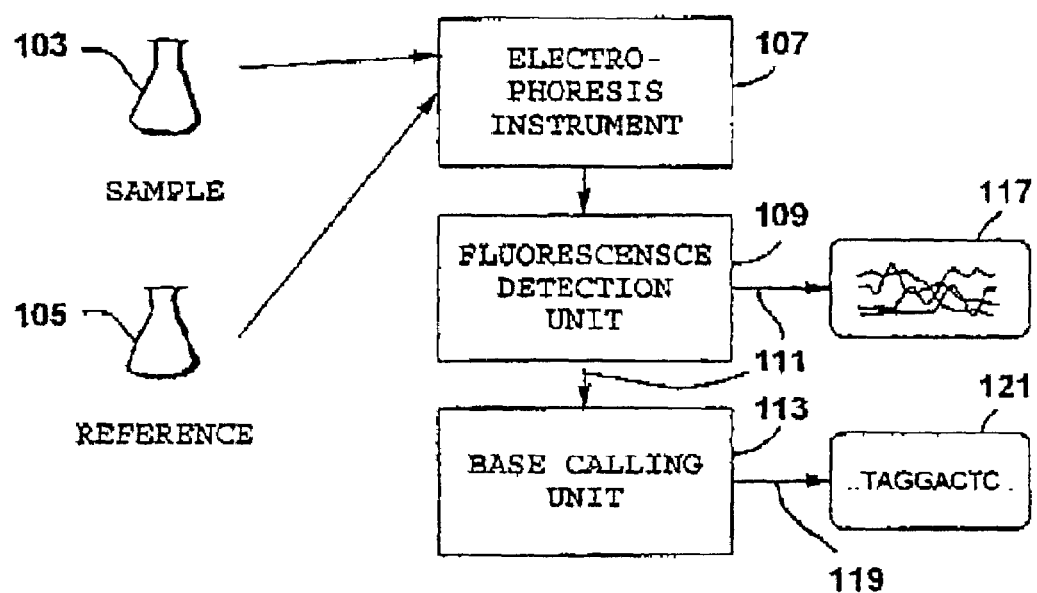
FIG. 3 is a schematic block diagram illustrating a system to produce data signals for analysis in accordance with the teachings herein.

FIG. 3 illustrates components of an embodiment of instrument system, including electrophoresis and fluorescence detecting instruments, to produce data signals to be analyzed in accordance with the teachings herein. It should be understood that suitable interfaces between the separate components, e.g., to adapt them for the transfer of information between the units, are included in the components, respectively.

According to FIG. 3, sample 103 and reference 105 polynucleotide solutions, properly prepared for the electrophoresis and fluorescence detection, are added to the electrophoresis instrument 107 for separation into detectable components. During or after the separation, the components are detected by fluorescence emitted when excited by an excitation beam; e.g., laser light.

The fluorescence detection unit 109 produces signals 111, representing the intensity levels of fluorescence for the respective nucleotide bases of the sample and reference sequence, respectively. The intensity signals 111 are output to a base calling unit 113, and may also be sent to an output or storage device 117, such as a display device (monitor), a printer or disk drive.

The base calling unit 113, employing the teachings herein, interprets the intensity signals 111 and provides output corresponding to sequences of nucleotide bases 121. It should be appreciated that the base calling unit 113 may specifically label one or more positions in a sequence that are not determined with sufficiently high confidence.

Computer Implementation

Figure 4:
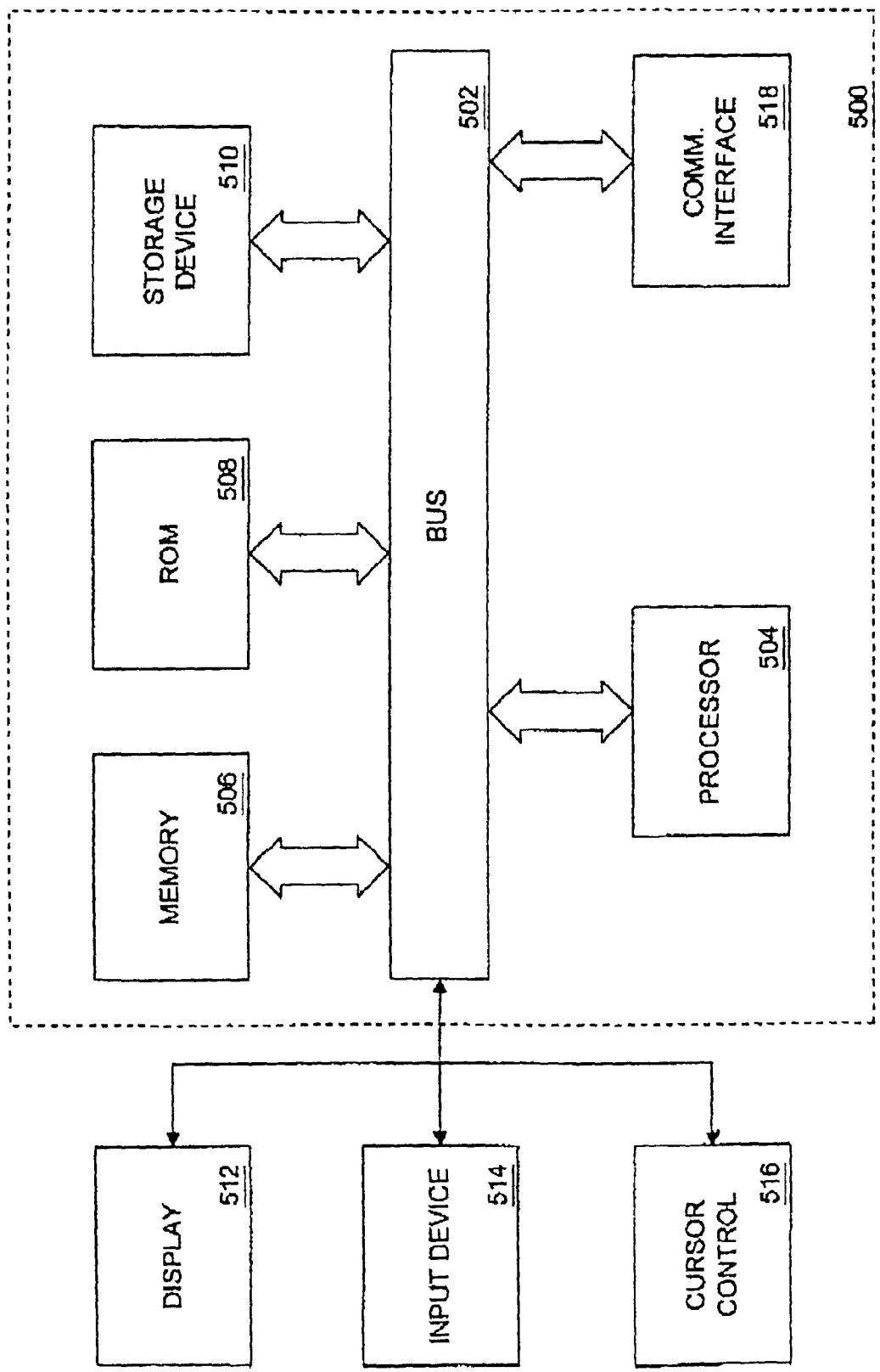
FIG. 4 is a block diagram that illustrates a computer system, according to various embodiments, upon which embodiments of the present teachings may be implemented.

FIG. 4 is a block diagram that illustrates a computer system 500, according to certain embodiments, upon which embodiments of the present teachings may be implemented. Computer system 500 includes a bus 502 or other communication mechanism for communicating information, and a processor 504 coupled with bus 502 for processing information. Computer system 500 also includes a memory 506, which can be a random access memory (RAM) or other dynamic storage device, coupled to bus 502 for determining base calls, and instructions to be executed by processor 504. Memory 506 also may be used for storing temporary variables or other intermediate information during execution of instructions to be executed by processor 504. Computer system 500 further includes a read only memory (ROM) 508 or other static storage device coupled to bus 502 for storing static information and instructions for processor 504. A storage device 510, such as a magnetic disk or optical disk, is provided and coupled to bus 502 for storing information and instructions.

Computer system 500 may be coupled via bus 502 to a display 512, such as a cathode ray tube (CRT) or liquid crystal display (LCD), for displaying information to a computer user. An input device 514, including alphanumeric and other keys, is coupled to bus 502 for communicating information and command selections to processor 504. Another type of user input device is cursor control 516, such as a mouse, a trackball or cursor direction keys for communicating direction information and command selections to processor 504 and for controlling cursor movement on display 512. This input device typically has two degrees of freedom in two axes, a first axis (e.g., x) and a second axis (e.g., y), that allows the device to specify positions in a plane.

A base call is provided by computer system 500 in response to processor 504 executing one or more sequences of one or more instructions contained in memory 506. Such instructions may be read into memory 506 from another computer-readable medium, such as storage device 510. Execution of the sequences of instructions contained in memory 506 causes processor 504 to perform the process states described herein. Alternatively hard-wired circuitry may be used in place of or in combination with software instructions to implement the present teachings. Thus implementations of the present teachings are not limited to any specific combination of hardware circuitry and software.

The term "computer-readable medium" as used herein refers to any media that participates in providing instructions to processor 504 for execution. Such a medium may take many forms, including but not limited to, non-volatile media, volatile media, and transmission media. Non-volatile media includes, for example, optical or magnetic disks, such as storage device 510. Volatile media includes dynamic memory, such as memory 506. Transmission media includes coaxial cables, copper wire, and fiber optics, including the wires that comprise bus 502. Transmission media can also take the form of acoustic or light waves, such as those generated during radio-wave and infra-red data communications.

Common forms of computer-readable media include, for example, a floppy disk, a flexible disk, hard disk, magnetic tape, or any other magnetic medium, a CD-ROM, any other optical medium, punch cards, papertape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 504 for execution. For example, the instructions may initially be carried on magnetic disk of a remote computer. The remote computer can load the instructions into its dynamic memory and send the instructions over a telephone line using a modem. A modem local to computer system 500 can receive the data on the telephone line and use an infra-red transmitter to convert the data to an infra-red signal. An infra-red detector coupled to bus 502 can receive the data carried in the infra-red signal and place the data on bus 502. Bus 502 carries the data to memory 506, from which processor 504 retrieves and executes the instructions. The instructions received by memory 506 may optionally be stored on storage device 510 either before or after execution by processor 504.

EXAMPLES

The following examples are merely illustrative and are not intended in any manner to limit the scope of the present invention or of the claims directed thereto.

Example 1

FIG. 1 is an electropherogram representing data from a simulated 5th-dye run. The x-axis is scan number, and the y-axis is fluorescent amplitude, in arbitrary units. Each scan is approximately 1 second in duration. Most of the peaks are equally spaced, i.e., they occur at each 18 bases. A mobility similar to 3700 POP5 data (Applied Biosystems; Foster City, Calif.) was used to simulate realistic scan spacing. A few of the peaks deviate from the regular 18-base spacing. Such patterned peaks are used to provide absolute calibration of the start position, i.e., base 1. For ease of identification, regularly spaced peaks are identified by open (red) circles, whereas patterned peaks are identified with closed (green) circles.

From the 5th dye ladder (FIG. 1A) the curves of FIGS. 1B and 1C can be estimated. FIG. 1B represents the spacing peak-to-peak as a function of scan number. The spacing is also reported in scan number. The curve of FIG. 1C represents the width of each peak, in scan number, as a function of scan number. The width can be measured as the full width at half the peak's maximum height (FWHM).

The width curve (FIG. 1C) can be used to improve deconvolution techniques. Several techniques, such as Wiener and Maximum Entropy, perform Fourier transforms on a window in which the peak width is relatively constant. By reinterpolating the scan axis to achieve a constant width, the Fourier window can be the entire data set. This will lead to significantly improved execution time and eliminate the need to stitch deconvolved windows together.

Example 2

FIG. 2 provides a flowchart showing steps contemplated by an embodiment of the present invention.

Peak detection can be achieved through a number of techniques known in the art. For example, peak detection can be achieved via identification of local maxima in the discretely sampled EP data. An embodiment of the present invention makes use of an algorithm that involves Savitsky-Golay smoothing. Any of a variety of techniques for estimation of peak characteristics can be employed in practicing the present invention. Characteristics of interest include: position (scan), and shape (e.g., height, width). Savitsky-Golay smoothing can also be used toward these ends.

Peak discrimination can also be achieved in a variety of ways. In various embodiments, the Euclidean distances in height-width space of peaks from some reference point are sorted and differenced to determine a boundary that separates peaks to be ignored from those to be considered for subsequent analysis.

Matching peaks with sizes from the size definition can be handled by RatioMatcher, a dynamic programming algorithm designed for such a task (see U.S. Provisional Patent Application Ser. No. 60/219,697; incorporated herein by reference). As the present invention will often involve dealing with relatively large numbers of sizes and peaks, RatioMatcher may in some circumstances be more computationally intensive than desired. However, RatioMatcher can be used on a subset of the data and then that result can be used as a starting point for a simpler algorithm that exploits specific characteristics of the $5^{th}$-dye data (e.g., well resolved, nearly equally-spaced peaks).

The results of the analysis of the $5^{th}$-dye data aid the processing and analysis of the primary 4 dye signals and the classification of peaks (i.e., calling bases). Advantages include:

The well resolved peaks in the $5^{th}$-dye signal will provide good estimates of peak shape (width as well as non-uniform effects due to loading/injection anomalies, bubbles in the separation matrix, etc.) and spacing as a function of position in the signal. These width and spacing estimates will enable better analysis of associated signals with poor resolution.

Mobility shift calibrations depend on the location of a reference point, usually called "base 1". Estimation of this reference point will be improved by the size-scan map provided by the $5^{th}$-dye signal analysis.

Example 3

According to one example of the present teachings, a ladder is designed and constructed to contain a $5^{th}$ dye-labeled fragment every 10 to 20 bases from base ~20 to base ~1200-1500 (i.e., at least 60 fragments). An additional 2-3 peaks can be designed to occur near the beginning for base 1 estimation. The ladder sequence, in this embodiment, exhibits generally "normal" migration (e.g., by having fairly equal representation of all 4 bases), and does not exhibit substantial mobility irregularities when run under standard conditions. The ladder can be comprised of, for example, of a repeating internal unit, so between peaks there will be a constant number of bases of the same sequence. The ladder can be generated, for example, from a single-base sequencing reaction. In another embodiment, the template includes additional peaks, but contains isolated peaks (by at least ~5 bases) every ~20 or so bases. Ideally it comprises the repeating unit described above.

Example 4

This example contemplates two different types of products: (a) a set of nucleic acid sequences that are synthesized (and ligated), and (b) a set of nucleic acid sequences that are synthesized and cloned. Product (a) is comprised of (5' end labeled) $5^{th}$ dye-labeled fragments of varying sizes, which will generate a $5^{th}$ dye ladder when run, for example, on a 3700 or 3100 DNA Analyzer (Applied Biosystems; Foster City, Calif.). Product (b) is a clone which may be used to generate a (3' end labeled) $5^{th}$ dye ladder when sequenced with a $5^{th}$ dye-labeled dideoxy terminator, using, for example, the—21M13 universal primer.

The $5^{th}$ dye ladder can be run with sequencing samples, for example, on ABI DNA Analyzer instruments. The ladder can range in size, for example, from 18 or 19 to >7200 bases, with one $5^{th}$ dye labeled fragment every 10 to 50 bases (e.g., every 12 or 18 bases, or so).

In embodiments of product (a) or (b), there are 3 additional $5^{th}$ dye-labeled fragments generated by the $5^{th}$ dye terminator sequencing reaction, at around bases 57, 87, and 94.

Example 5

An internal calibration standard is generated comprising a sequence having three bases (e.g., any three of G, C, A, T) incorporated randomly along the length of the sequence and a fourth base (e.g., the fourth of G, C, A, T) is incorporated at (and only at) regularly spaced intervals along the length of the sequence, e.g., every 10th base position. The fourth base is labeled with a unique fluorescent label using standard sequencing reactions.

Example 6

This example relates to a 5th-dye ladder constructed in a fashion like that described above in connection with Product (b) of Example 4.

Figure 5:
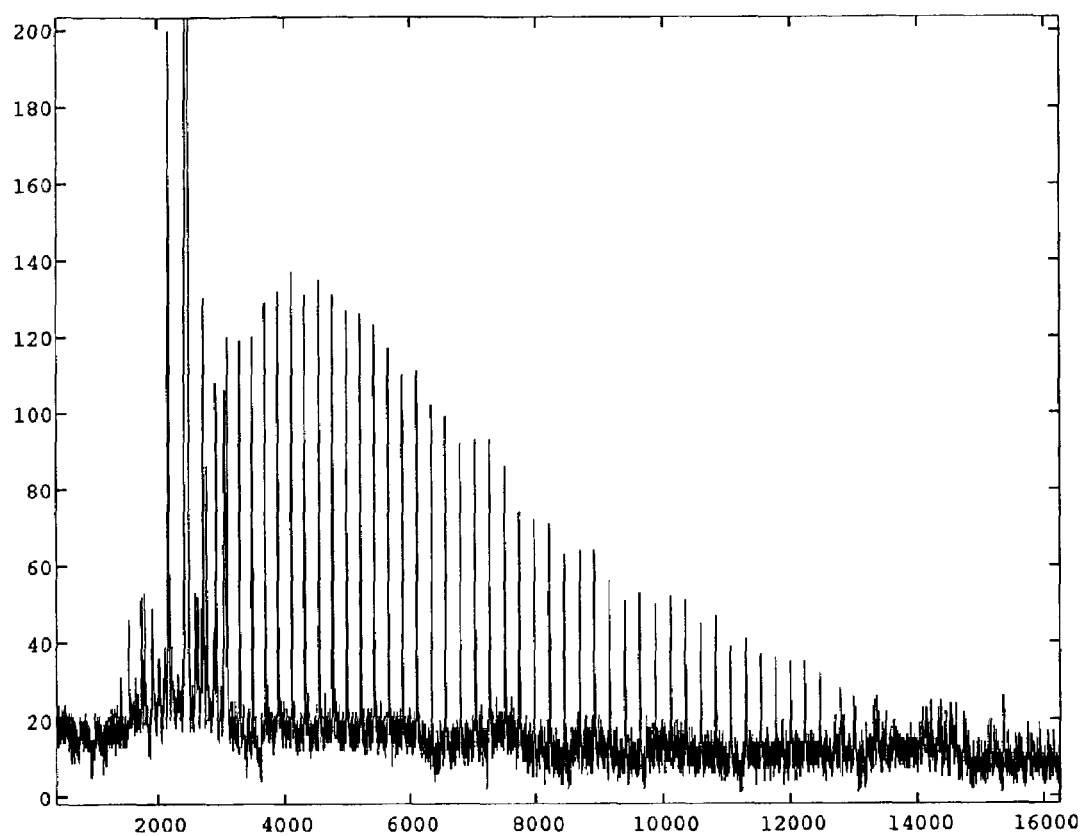
FIG. 5 is an electrophoretic profile of a 5th-dye ladder, constructed according to various embodiments, using an automated DNA Analyzer. The x-axis is scan number, and the y-axis is fluorescent amplitude.

An original cloning insert (small volumes) was created by autoligation of a 12-mer that contained only one G, which occurs at the end of the 12-mer. Larger quantities were produced by cloning the ligation product. Then a regular 4 dye sequencing reaction was run on the clone product. FIG. 5 is a plot showing only the G trace from the sequencing data. The axes on the plot as shown have been clipped a bit to zoom in on the more pertinent and useful part.

Example 7

This example relates to sample injection/loading monitoring.

Figure 6A:
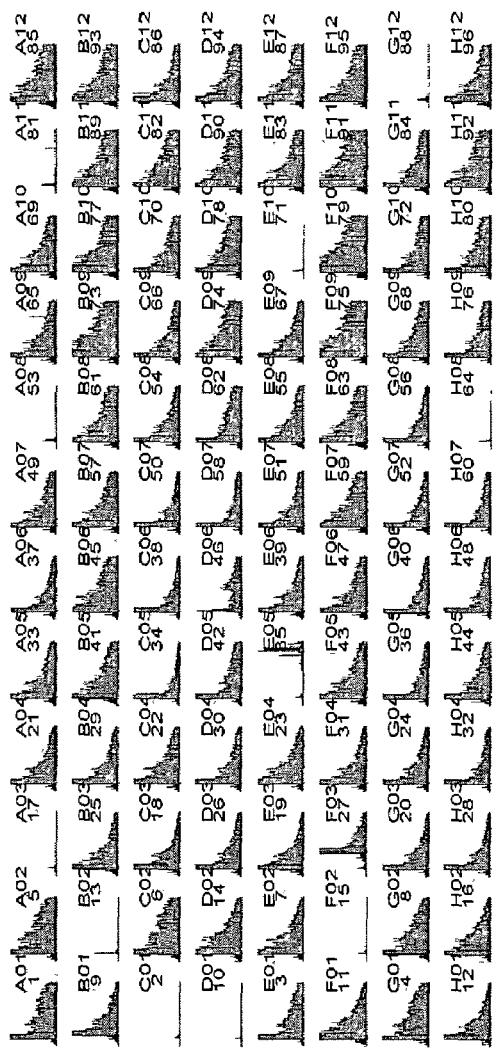
FIG. 6 illustrates signals reported from an ABI Prism 3700 DNA Analyzer instrument for each of 96 sequencing samples, each of which was combined with a set of 5th dye fragments. For each well, the upper panel shows sequencing signals (dyes one through four) and the lower panel shows 5th dye signal.
Figure 6B:
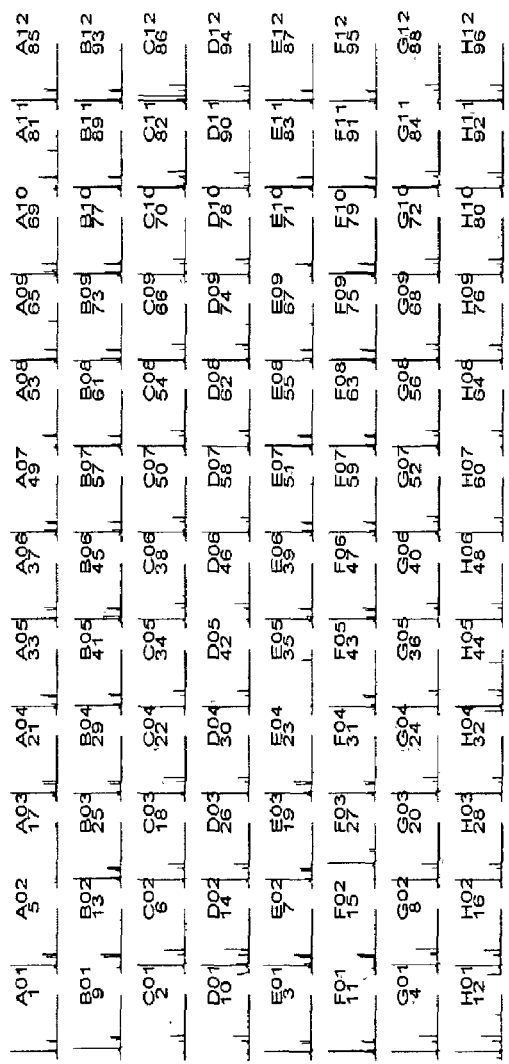
Figure 7:
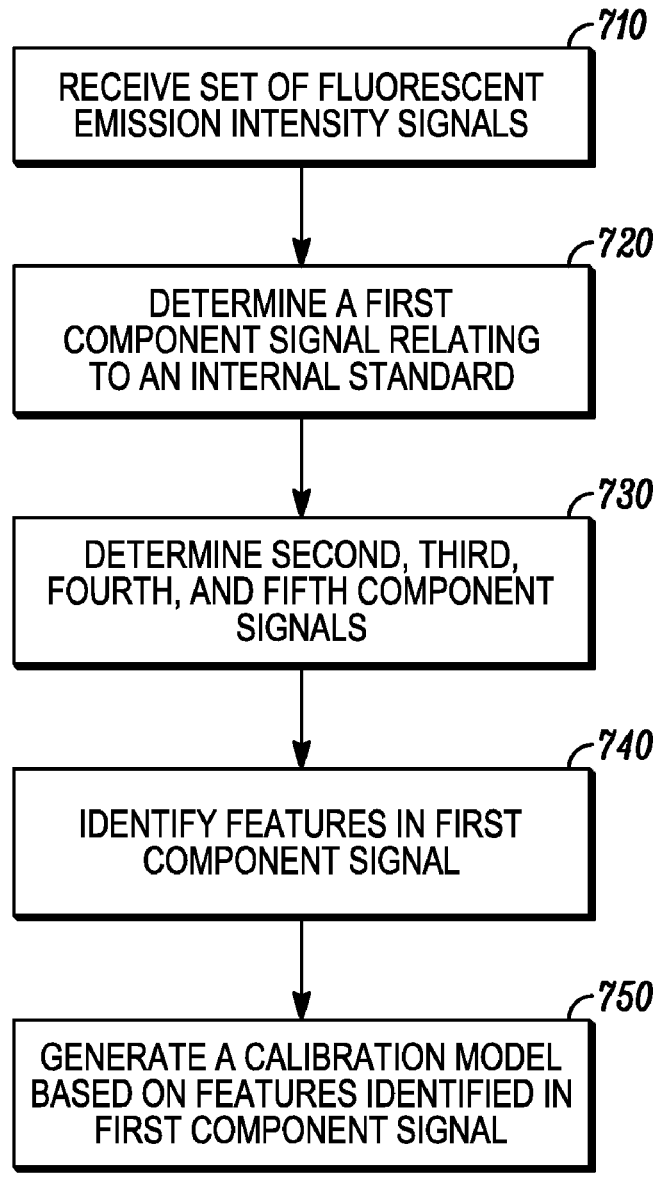
FIG. 7 illustrates certain functional elements contemplated by various embodiments of the present teachings.

Ninety-six sequencing samples were each combined with a set of 5th dye fragments. These samples were then loaded and run (separated) on an ABI Prism 3700 DNA Analyzer instrument and signals were collected. FIG. 6 illustrates the signals reported from the 3700 instrument for each of these samples. The sample integrity can be determined by inspecting each sample result individually. In this Figure, the sample in the C01 position did not show any sequencing signal (dyes one through four) but the 5th dye signal was present. This indicates that there is no sequencing reaction product in C01, indicating a problem at the reaction stage of the process. On the other hand, profile A03 showed no signal in both the sequencing and 5th dye signals. This indicates a sample loading (injection) problem may have occurred. The E05 position showed both sequencing and $5^{th}$ dye signal, but each was slow to appear relative to their profiles in the other experiments. This may indicate problems in the capillary or loading well or even the sample purity.

All publications and patent applications referred to herein are hereby incorporated by reference to the same extent as if each individual publication or patent application was specifically and individually indicated to be incorporated by reference.

Those having ordinary skill in the art will understand that many modifications are possible. All such modifications are intended to be encompassed herein.

It is claimed:

1. A program storage device readable by a machine, embodying a program of instructions executable by the machine to perform method steps for calibration of polynucleotide sequence data, said method steps comprising:
    (i) receiving a set of fluorescent emission intensity signals where each of said fluorescent emission intensity signals of said set is comprised of a plurality of component signals, with each of said component signals representing a respective nucleotide base or an internal standard in a multicomponent mixture including a plurality of analyte polynucleotide fragments of unknown nucleotide sequence;
    (ii) determining a first component signal corresponding to the internal standard;
    (iii) determining a second, third, fourth and fifth component signal representing the respective nucleotide bases;
    (iv) identifying features from said first component signal and determining at least one peak-shape characteristic thereof,
    (v) generating a calibration model based at least in part on said at least one characteristic, and applying said calibration model to said second, third, fourth and fifth component signals, and
    (vi) reporting the result of applying said calibration model to said second, third, forth and fifth component signals to a user.

* * * * *